US010888235B2

(12) United States Patent
Hagfors et al.

(10) Patent No.: US 10,888,235 B2
(45) Date of Patent: Jan. 12, 2021

(54) SYSTEM, METHOD, AND APPARATUS FOR VISUALIZING CARDIAC TIMING INFORMATION USING ANIMATIONS

(71) Applicant: St. Jude Medical, Cardiology Division, Inc., St. Paul, MN (US)

(72) Inventors: Mark Hagfors, North Oaks, MN (US); Michael A. Quinn, St. Paul, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 341 days.

(21) Appl. No.: 15/537,524

(22) PCT Filed: Jan. 4, 2016

(86) PCT No.: PCT/US2016/012030
§ 371 (c)(1),
(2) Date: Jun. 19, 2017

(87) PCT Pub. No.: WO2016/111920
PCT Pub. Date: Jul. 14, 2016

(65) Prior Publication Data
US 2017/0360319 A1    Dec. 21, 2017

Related U.S. Application Data

(60) Provisional application No. 62/100,410, filed on Jan. 7, 2015.

(51) Int. Cl.
*A61B 5/04*        (2006.01)
*A61B 5/00*        (2006.01)
(Continued)

(52) U.S. Cl.
CPC .......... *A61B 5/04011* (2013.01); *A61B 5/044* (2013.01); *A61B 5/743* (2013.01); *A61B 5/0422* (2013.01)

(58) Field of Classification Search
CPC ...... A61B 5/04011; A61B 5/044; A61B 5/743
See application file for complete search history.

(56) References Cited

U.S. PATENT DOCUMENTS 5,697,377 A    12/1997    Wittkampf
5,983,126 A    11/1999    Wittkampf
(Continued)

FOREIGN PATENT DOCUMENTS

EP    2 638 853        9/2013
EP    2638853    *    9/2013    ............... A61B 5/04
(Continued)

OTHER PUBLICATIONS

International Search Report and Written Opinion for PCT/US2016/012030, dated Apr. 12, 2016.
(Continued)

*Primary Examiner* — Eric D Bertram
(74) *Attorney, Agent, or Firm* — Wiley Rein LLP

(57) ABSTRACT

An animated electrophysiology map is generated from a plurality of data points, each including measured electrophysiology information, location information, and timing information. The electrophysiology and location information can be used to generate the electrophysiology map, such as a local activation time, peak-to-peak voltage, or fractionation map. Animated timing markers can be superimposed upon the electrophysiology map using the electrophysiology, location, and timing information. For example a series of frames can be displayed sequentially, each including a static image of the electrophysiology map at a point in time and timing markers corresponding to the state or position of an activation wavefront at the point in time superimposed thereon. The visibility or opacity of the timing markers can be adjusted from frame to frame, dependent upon a distance between the timing marker and the activation wavefront, to (Continued)

give the illusion that the timing markers are moving along the electrophysiology map.

11 Claims, 22 Drawing Sheets

(51) Int. Cl.
*A61B 5/044* (2006.01)
*A61B 5/042* (2006.01)

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2006/0058624 A1 | 3/2006 | Kimura |
| 2011/0144510 A1* | 6/2011 | Ryu ............... A61B 5/042 600/509 |
| 2013/0245460 A1* | 9/2013 | King ............... A61B 5/743 600/476 |
| 2014/0200874 A1 | 7/2014 | Zeng et al. |

FOREIGN PATENT DOCUMENTS

| | | | | |
|---|---|---|---|---|
| JP | 2009-539566 | | 11/2009 | |
| JP | 2012-508079 | | 4/2012 | |
| WO | 01/34026 | | 5/2001 | |
| WO | WO 01/34026 | * | 5/2001 | ............. A61B 5/042 |
| WO | 2010/054409 | | 5/2010 | |
| WO | WO 2010/054409 | * | 5/2010 | ............... G09G 5/00 |

OTHER PUBLICATIONS

Jamil-Copley et al., 21 Novel Technologies for Mapping and Ablation of Complex Arrhythmias, Cardiac Arrhythmias—New Considerations, 2012, pp. 443-460.

Jamil-Copley et al., Application of Ripple Mapping with an Electroanatomic Mapping System for Diagnosis of Atrial Tachycardias, Journal of Cardiovascular Electrophysiology, 2013, vol. 24, No. 12, 1361-1369.

Linton et al., Cardiac ripple mapping: A novel three-dimensional visualization method for use with electroanatomic mapping of cardiac arrhythmias, Heart Rhythm, 2009, vol. 6, No. 12, 1754-1762.

* cited by examiner

SYSTEM, METHOD, AND APPARATUS FOR VISUALIZING CARDIAC TIMING INFORMATION USING ANIMATIONS

CROSS-REFERENCE TO RELATED APPLICATIONS

This application claims the benefit of U.S. provisional application No. 62/100,710, filed 7 Jan. 2015, which is hereby incorporated by reference as though fully set forth herein.

BACKGROUND

The present disclosure relates generally to electrophysiological visualization and mapping. More specifically, the present disclosure relates to a system, method, and apparatus for generating animated electrophysiological maps for visualizing cardiac timing information on the surface of a model.

Anatomical mapping, such as cardiac electrophysiological mapping, is used in numerous diagnostic and therapeutic procedures. In certain procedures, for example, various components associated with a depolarization wave are detected from electrogram signals obtained from a diagnostic catheter, and are used to generate a map, such as a local activation time ("LAT") map, a peak-to-peak ("PP") voltage map, or a complex fractionated electrogram ("CFE") map. Typically, such maps are static maps that employ colors and/or shading to represent parameters such as activation time, voltage, and degree of fractionation.

In some cases, it may be difficult to understand the directionality of cardiac activation wavefronts as they travel across the heart. Precise knowledge of this information is often important, however, to accurately discern patterns associated with certain cardiac arrhythmias. In some instances, such information may facilitate the detection of more complex rhythms that would otherwise be difficult to discern from more traditional, static maps.

BRIEF SUMMARY

Disclosed herein is a method of generating an animated electrophysiology map including the steps of: receiving a plurality of data points, each data point including measured electrophysiology information, location information, and timing information; generating an electrophysiology map using the electrophysiology information and location information of the plurality of data points; and superimposing an animation of a plurality of timing markers upon the electrophysiology map using the electrophysiology information, the location information, and the timing information for the plurality of data points.

According to aspects of the disclosure, the step of superimposing an animation of a plurality of timing markers upon the electrophysiology map includes generating a series of frames, each frame of the series of frames including: a static image of the electrophysiology map at a point in time; and one or more timing markers superimposed upon the static image of the electrophysiology map, the one or more timing markers corresponding to an activation wavefront at the point in time. The frames can be displayed in chronological sequence.

It is contemplated that a visibility, such as an opacity, of a timing marker of the one or more timing markers is related to a distance between a position of the activation wavefront on the electrophysiology map at the point in time and a position of the timing marker on the electrophysiology map. For example, the closer the timing marker is to the position of the activation wavefront, the more visible (e.g., the more opaque) the timing marker can be.

According to other aspects of the disclosure, the step of superimposing an animation of a plurality of timing markers upon the electrophysiology map includes depicting an activation wavefront moving across the electrophysiology map over time.

In still further aspects of the disclosure, the step of superimposing an animation of a plurality of timing markers upon the electrophysiology map includes: increasing a visibility of a first timing marker from a minimum visibility to a maximum visibility; decreasing the visibility of the first timing marker from the maximum visibility to the minimum visibility; increasing a visibility of a second timing marker from the minimum visibility to the maximum visibility; and decreasing the visibility of the second timing marker from the maximum visibility to the minimum visibility. Optionally, the steps of decreasing the visibility of the first timing marker and increasing the visibility of the second timing marker can occur concurrently (e.g., the first timing marker can be fading out as the second timing marker is fading in). Indeed, a first time period over which at least one of the step of increasing a visibility of the first timing marker and the step of increasing a visibility of a second timing marker occurs can be shorter than a second time period over which at least one of the step of decreasing the visibility of the first timing marker and the step of decreasing the visibility of the second timing marker occurs.

Various electrophysiology maps, including local activation timing maps, activation timing propagation maps, peak-to-peak voltage maps, and fractionation maps are contemplated. Likewise, the plurality of timing markers can include a plurality of maximum voltage over time markers.

Also disclosed herein is a method of generating an animated map of a cardiac activation wavefront, including: receiving a plurality of data points, wherein each data point of the plurality of data points includes location information and activation timing information; displaying a model of a portion of a cardiac surface; and sequentially displaying a plurality of time markers corresponding to the plurality of data points over a playback time period, wherein, for each time marker of the plurality of time markers: a time marker display location is determined by the location information for a respective data point of the plurality of data points, and a time marker display sequence is determined by the activation timing information for the respective data point of the plurality of data points. The model of a portion of the cardiac surface can include an electrophysiology map of the portion of the cardiac surface.

In further embodiments, for each time marker of the plurality of time markers, the time marker has a maximum visibility time during the playback time period determined by the activation timing information for the respective data point of the plurality of data points, the time marker fades in starting at a fade in initiation time preceding the maximum visibility time, and the time marker fades out starting at the maximum visibility time and ending at a fade out completion time following the maximum visibility time. The fade in initiation time can precede the maximum visibility time by a first time period, and the fade out completion time can follow the maximum visibility time by a second time period longer than the first time period.

According to another embodiment disclosed herein, a system for superimposing an animated timing sequence onto an electrophysiological map includes: computer configured to: receive a plurality of three-dimensional data points each including timing activation information; generate an electrophysiological map on a display screen based on the plurality of three-dimensional data points; initiate a playback animation to generate a sequence of cardiac timing activation frames over time, each frame including an active timing marker; and superimpose, for each frame, the active timing marker onto the electrophysiological map; wherein the computer is configured to adjust an opacity of the active timing marker on the display screen based on a current time of the playback animation. The computer can also be configured to adjust the opacity of the active timing marker to fade in to a maximum opacity and to fade out from the maximum opacity based on a current time of the playback animation.

The foregoing and other aspects, features, details, utilities, and advantages of the present invention will be apparent from reading the following description and claims, and from reviewing the accompanying drawings.

DETAILED DESCRIPTION

The present disclosure provides systems, methods, and apparatus for the creation of electrophysiology maps (e.g., electrocardiographic maps). For purposes of illustration, several exemplary embodiments will be described in detail herein in the context of cardiac electrophysiology. It is contemplated, however, that the systems, methods, and apparatuses, described herein can be utilized in other contexts.

Figure 1:
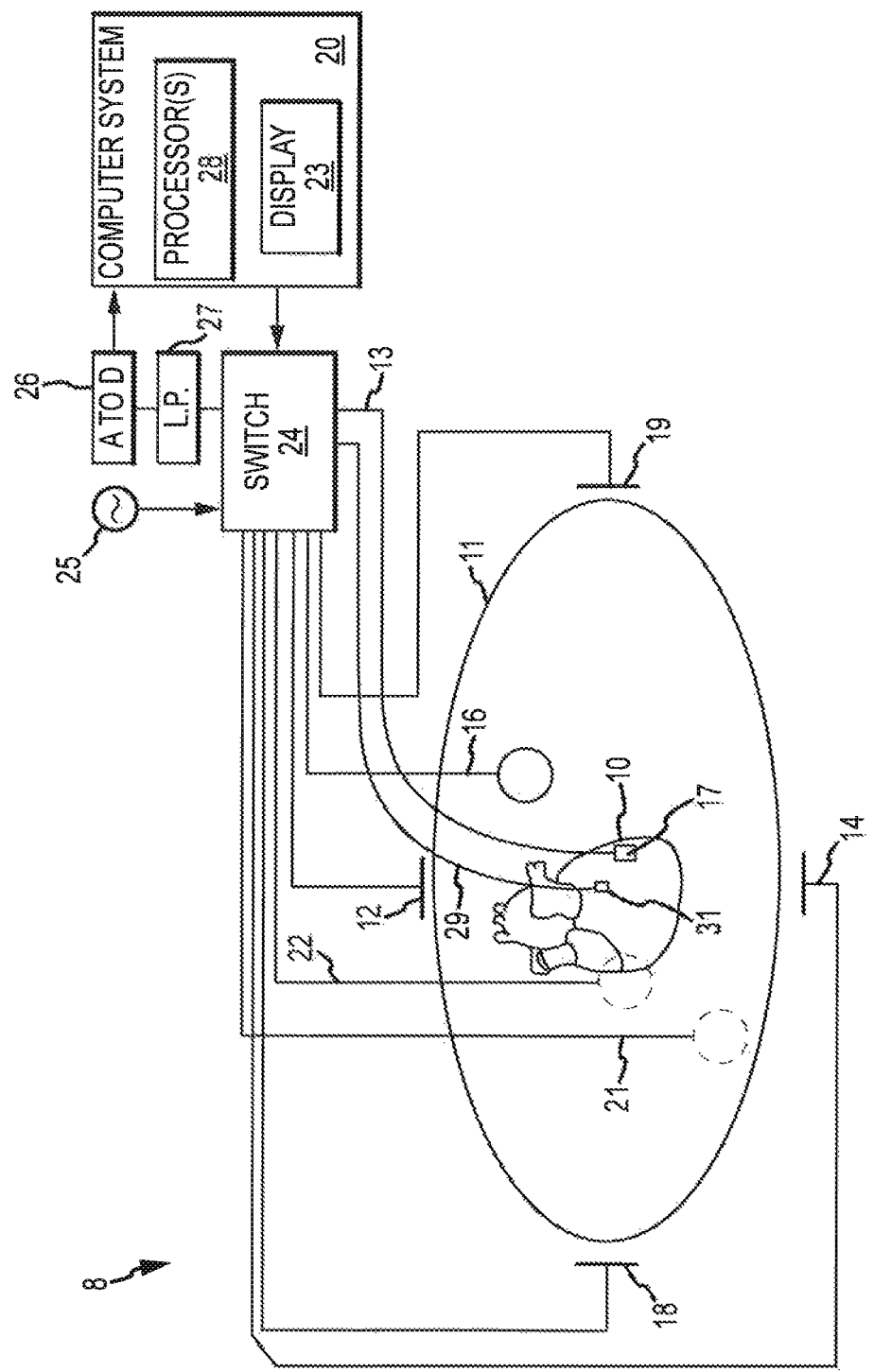
FIG. 1 is a schematic diagram of an exemplary electroanatomical mapping system, such as may be used in an electrophysiology study.

FIG. 1 shows a schematic diagram of an exemplary system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10. In some embodiments, and as discussed further herein, the system 8 can be used to generate animated electrophysiology maps that can be used to better visualize cardiac timing information over a period of time, allowing a clinician to better visualize and assess conduction velocity patterns across the surface of the heart 10. In some embodiments, for example, animated cardiac timing information can be superimposed onto another map such as a local activation timing (LAT) propagation map, a peak-to-peak voltage map, and/or a fractionated electrogram map to aid the clinician in determining the source of an arrhythmia.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, the leads and their connections to computer 20 are not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise sixty-four electrodes on twelve catheters disposed within the heart and/or vasculature of the patient. Of course, this embodiment is merely exemplary, and any number of electrodes and catheters may be used within the scope of the present invention. Likewise, it should be understood that catheter 13 (or multiple such catheters) are typically introduced into the heart and/or vasculature of the patient via one or more introducers (not shown in FIG. 1, but readily understood by the ordinarily skilled artisan).

Figure 2:
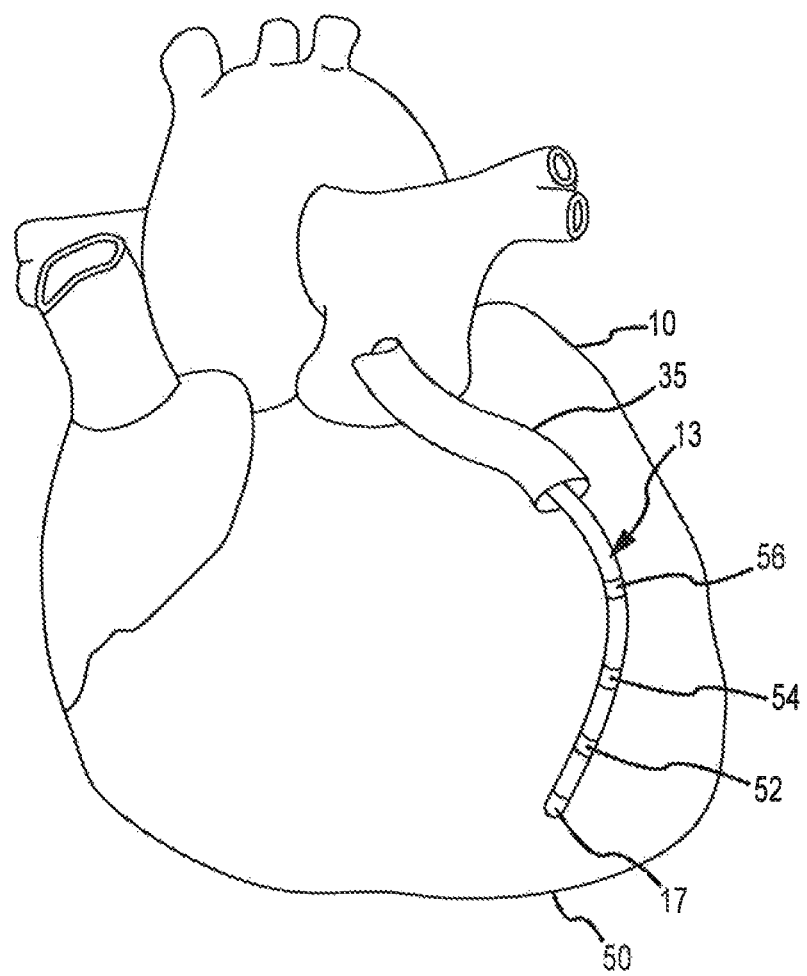
FIG. 2 depicts an exemplary catheter that can be used in an electrophysiology study.

For purposes of this disclosure, a segment of an exemplary catheter 13 is shown in FIG. 2. Catheter 13 extends into the left ventricle 50 of the patient's heart 10 through an introducer 35, the distal-most segment of which is shown in FIG. 2. The construction of introducers, such as introducer 35, are well known and will be familiar to those of ordinary skill in the art, and need not be further described herein. Of course, catheter 13 can also be introduced into the heart 10 without the use of introducer 35.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, the system 8 is the EnSite™ Velocity™ cardiac mapping system of St. Jude Medical, Inc., which generates electrical fields as described above, or another localization system that relies upon electrical fields. Other localization systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation System, as well as MediGuide™ Technology from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

FIGS. 3A-3F are several screen shots of a graphical user interface (GUI) 100 that can be used in conjunction with the system 8 of FIG. 1 for generating an animated electrophysiology map in accordance with an exemplary embodiment of the present disclosure. The screen shots in FIGS. 3A-3F may represent, for example, several exemplary views generated by computer 20 that, when displayed as a sequence over a period of time (e.g., one or more cardiac cycles), depict an animation showing the timing of cardiac activations across the surface of a heart 10.

Figure 3A:
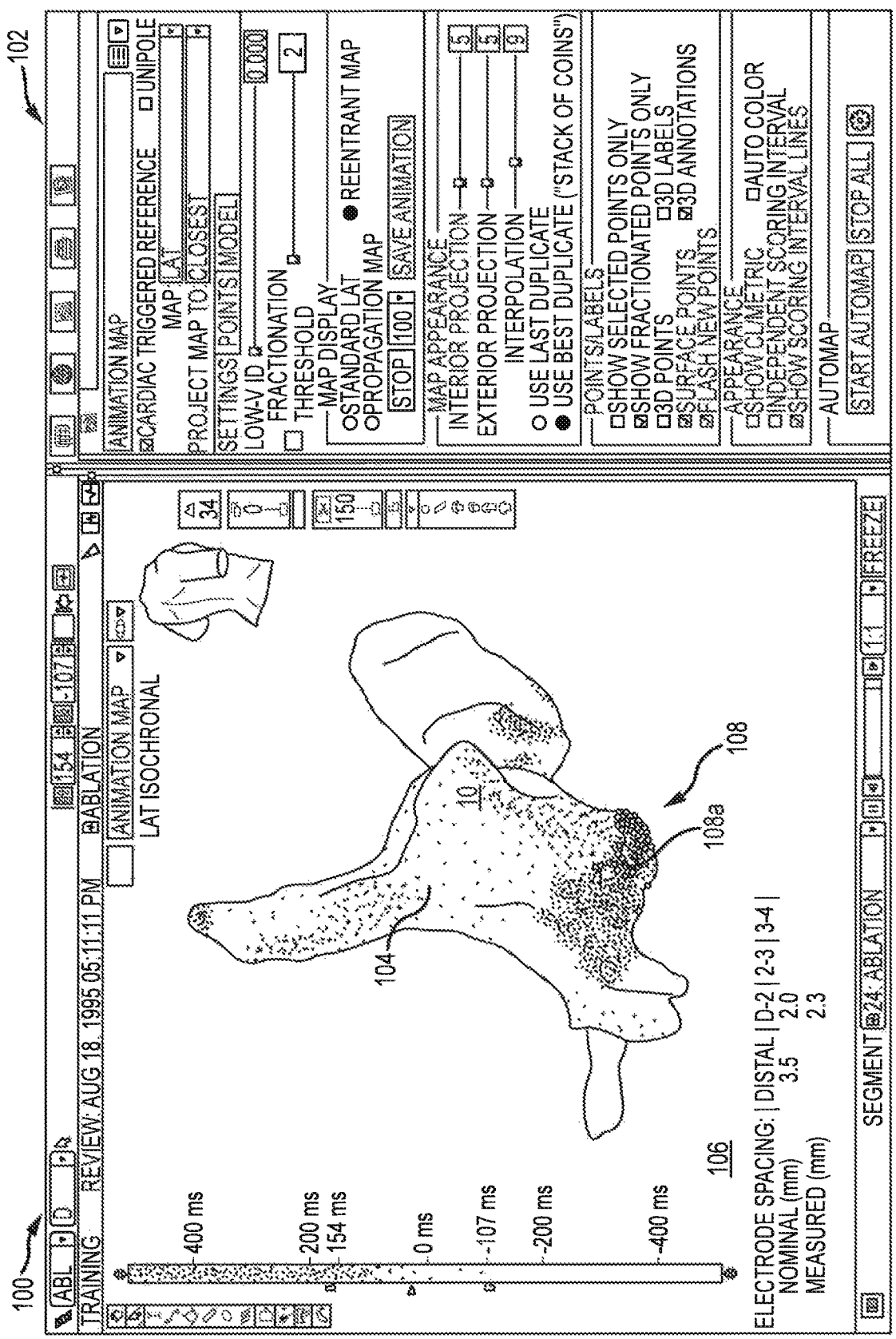
FIGS. 3A-3F are several screen shots of a graphical user interface used for generating an animated electrophysiology map in accordance with an exemplary embodiment of the present disclosure.

As can be seen in a first view in FIG. 3A, the GUI 100 includes a series of controls 102 that can be used for generating an electrophysiological map 104 on a display screen 106. In certain procedures, for example, the GUI 100 can be used for displaying a local activation timing (LAT) propagation map 104 on the model surface, as shown. The use of LAT maps 108 is generally known in electrophysiology procedures, and is thus not described in detail herein for sake of brevity. As can be seen in FIG. 3A, the LAT map 104 uses different colors across the surface of the model to depict the timing of cardiac activations, with relatively early activation times represented as white, red, or orange colors and relatively late activation times represented as blue, indigo, and violet colors on the map 104.

As can be further seen in FIG. 3A, the GUI 100 is further configured to display a sequence of timing markers 108 that can be used either alone or in conjunction with the LAT map 104 to provide the clinician with a better understanding of the timing sequence of cardiac activations. In some embodiments, the timing markers 108 may each comprise a large dot, point, or other suitable graphical representation that can be superimposed onto the display screen 106 over the LAT map 104, as shown. Each of the timing markers 108 may represent, for example, a voltage measured at a particular three dimensional location on the heart using a catheter such as catheter 13 described herein in conjunction with FIGS. 1-2. In some embodiments, for example, the timing markers 108 represent a maximum voltage as measured by one or multiple of the catheter electrodes 17, 52, 54, 56 during a single cardiac cycle, or across multiple cardiac cycles. As with the measurements used in generating the LAT map 104, the system 8 tracks the location of each discrete timing marker 108 and superimposes the marker 108 over the map 104. To ensure that the timing markers 104 visually standout from the colors used by the LAT map 104, the system 8 may assign a different color (e.g., neon green) to each timing marker 108.

FIGS. 3B-3F depict several additional views or frames showing the visualization of an activation sequence animation using the timing markers 108. As can be further understood with respect to FIGS. 3B-3F, the system 8 is configured to display an animation of an activation sequence by adjusting the opacity of each timing marker 108 over a playback time. During the playback of an animation, the timing markers 108 representative of the activation wavefront at a particular time are selectively displayed on the screen 106 whereas timing values that are not at or near the current playback time are removed from the screen 106. By comparison of FIG. 3B-3C, for example, which may represent a time difference in the cardiac cycle of approximately 20 ms, the location of the timing markers 108 can be seen to have shifted from a first location on the map 104 to a second location thereon. When viewed as a temporal sequence, the timing markers 108 appear to move across the surface of the map 104, providing an illusion that the markers 108 are in motion; a phenomenon similar to that of objects contained in individual frames of a motion picture.

This process of selectively displaying and removing the timing markers 108 in this fashion allows the clinician to better discern patterns and/or directionality that would otherwise not be apparent by interpreting between color bands on a static map such as a traditional LAT map. For instance, unlike a traditional LAT map, the ability to playback an animation of the timing markers 108 provides the clinician with an improved understanding of the directionality (and in some cases also the source) of the wavefront. In some instances, this may facilitate the detection of more complex rhythms that would otherwise be difficult to discern from a static map.

Figure 6:
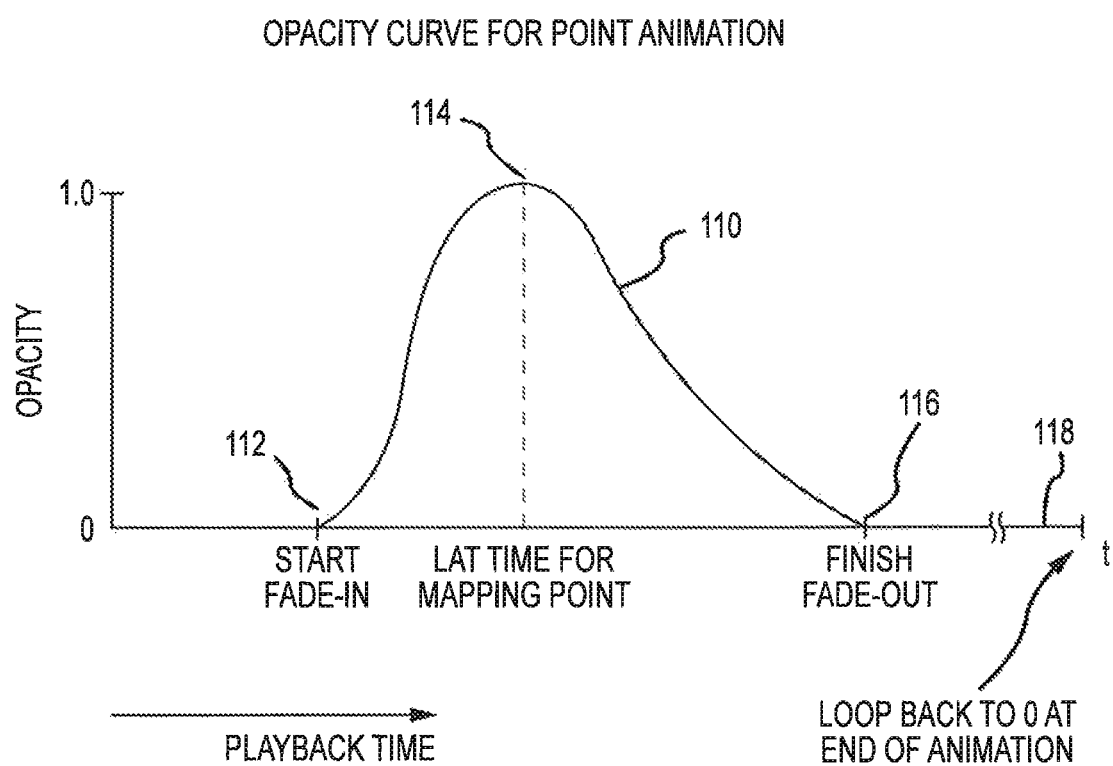
FIG. 6 is a graph showing the change in opacity state of a timing marker over time.

In some embodiments, the system 8 is configured to adjust a level of opacity of each of the timing markers 108 depending on the timing of the measurement relative to the current playback time. In certain embodiments, and as further shown in FIG. 6, the system 8 can be configured to adjust the opacity of the timing marker 108 between a first, invisible state to a second, bright state based on the LAT timing value associated with that marker 108. The opacity state of each of the timing markers 108 over time (t) can be represented graphically as a curve 110, beginning at time t=0 and ending at a later point t, which may represent the end of a full cardiac cycle or multiple such cycles. From an initial point 112 on the curve 110 to point 114 thereon, when the current playback time (t) is at or near the LAT time associated with the mapping point, the system 8 can be configured to gradually increase the opacity of the timing marker 108. At point 114 along the curve 110 when the timing marker 108 coincides with the current playback time, the marker 108 is at its greatest opacity (that is, at its maximum visibility). In similar fashion, the system 8 can be configured to fade-out or reduce the opacity of the timing marker 108 along the curve 110 until at point 116, when the timing marker 108 disappears completely from the screen (or is otherwise at its minimum visibility). In some embodiments, the fade-out time period (i.e., the time between the current playback time to point 116) is greater than the fade-in period (i.e., the time period between point 112 and the current playback time 114). For example, the fade-in period may comprise 6 ms whereas the fade-out period may comprise 44 ms.

At point 118 along the curve 110, the system 8 may then loop back to time t=0 and repeat the playback animation process one or more additional times, as desired. In use, the fading in and subsequent fading out of the timing markers 108 in this manner provides the clinician with a visual cue as to the activation pattern. This allows the clinician to better understand complex conduction patterns that may be present on the map.

Figure 3B:
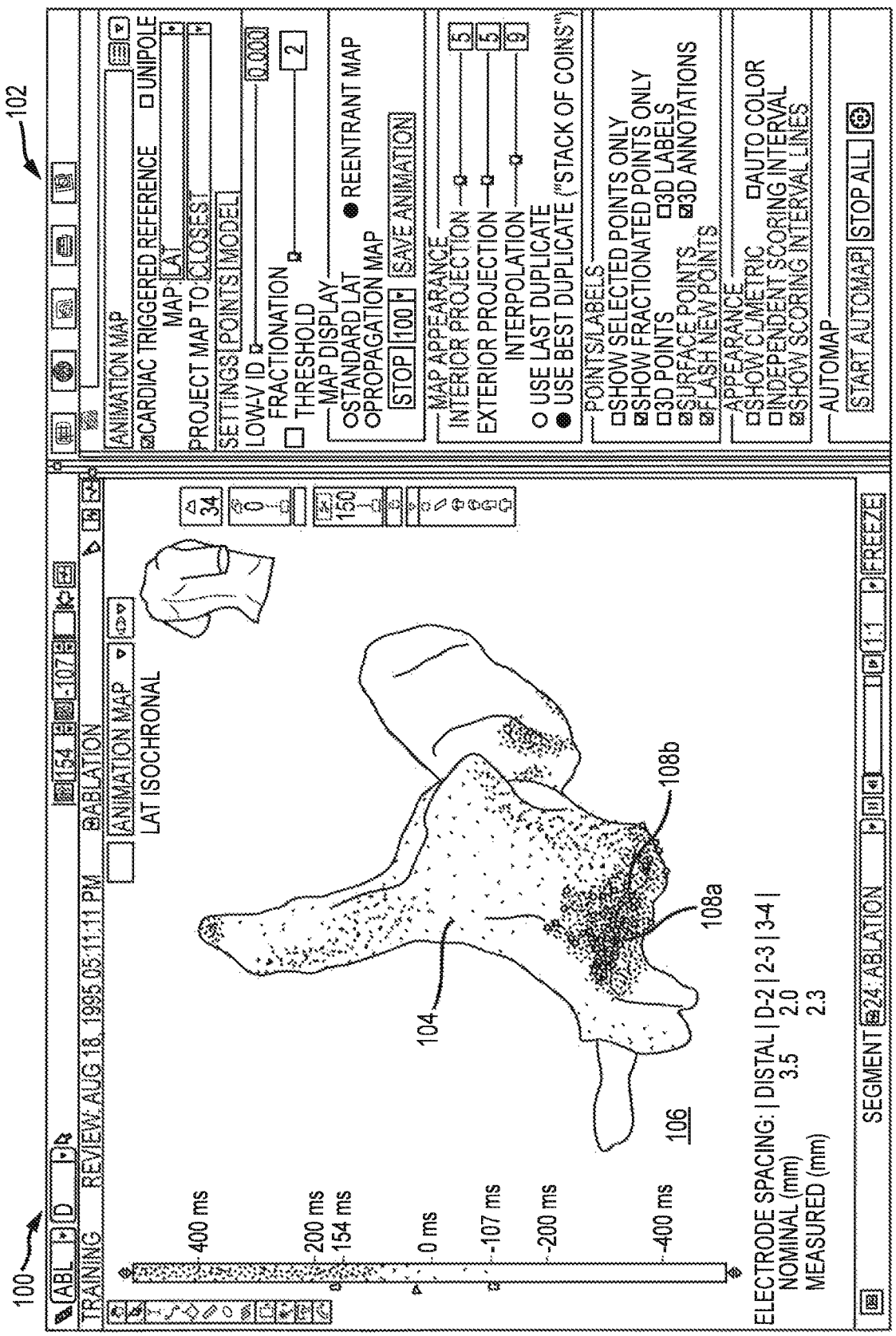
Figure 3C:
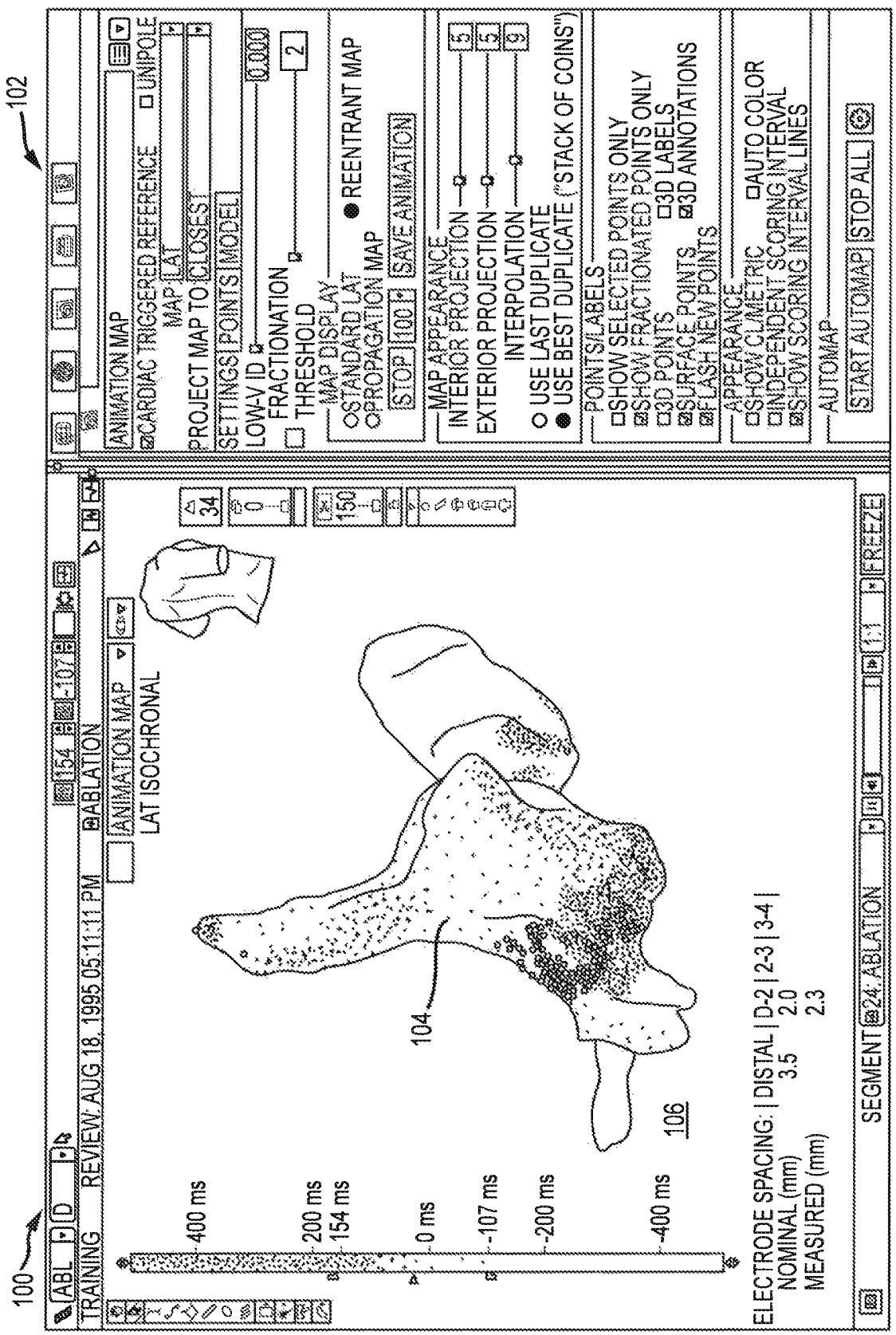
Figure 3D:
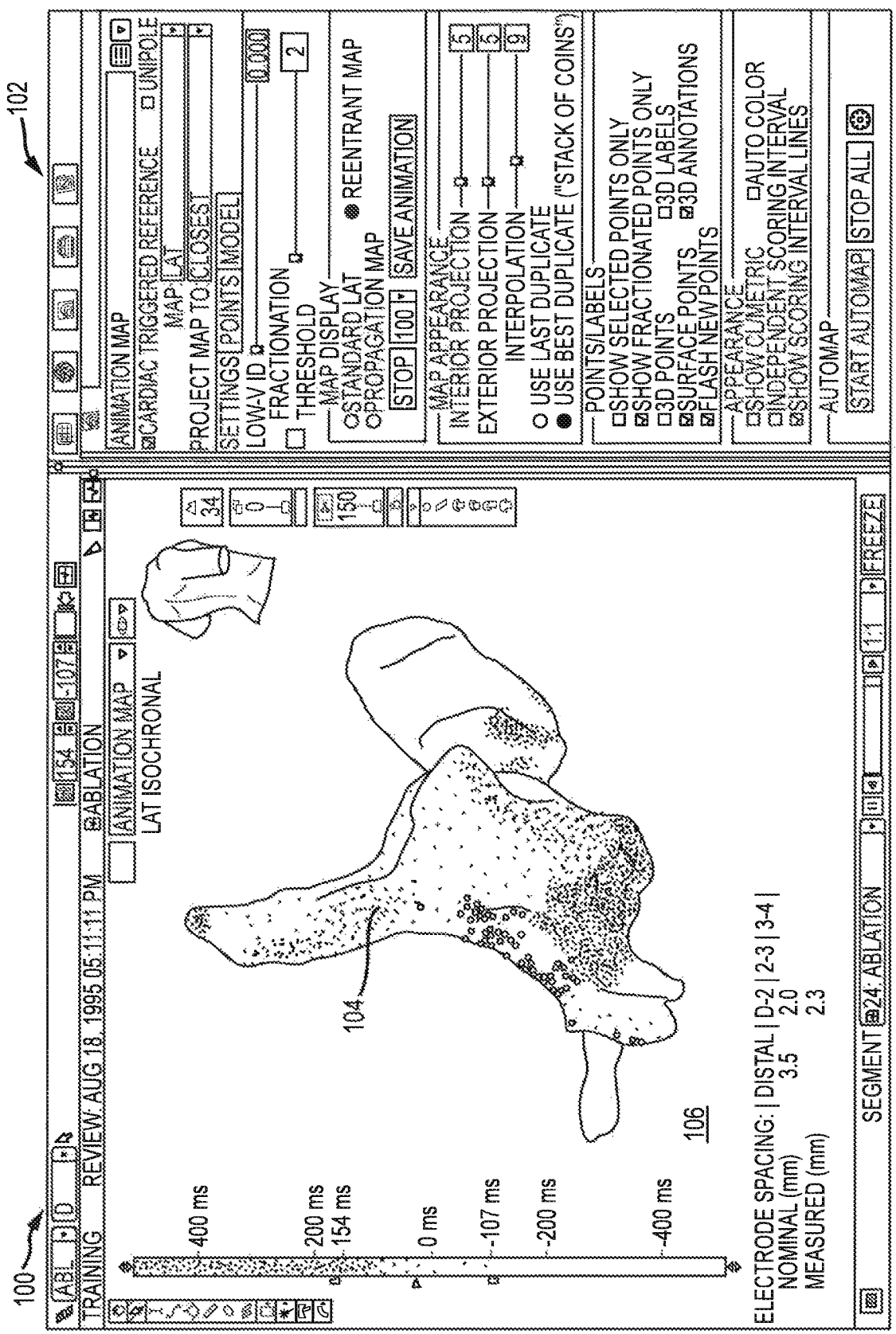
Figure 3E:
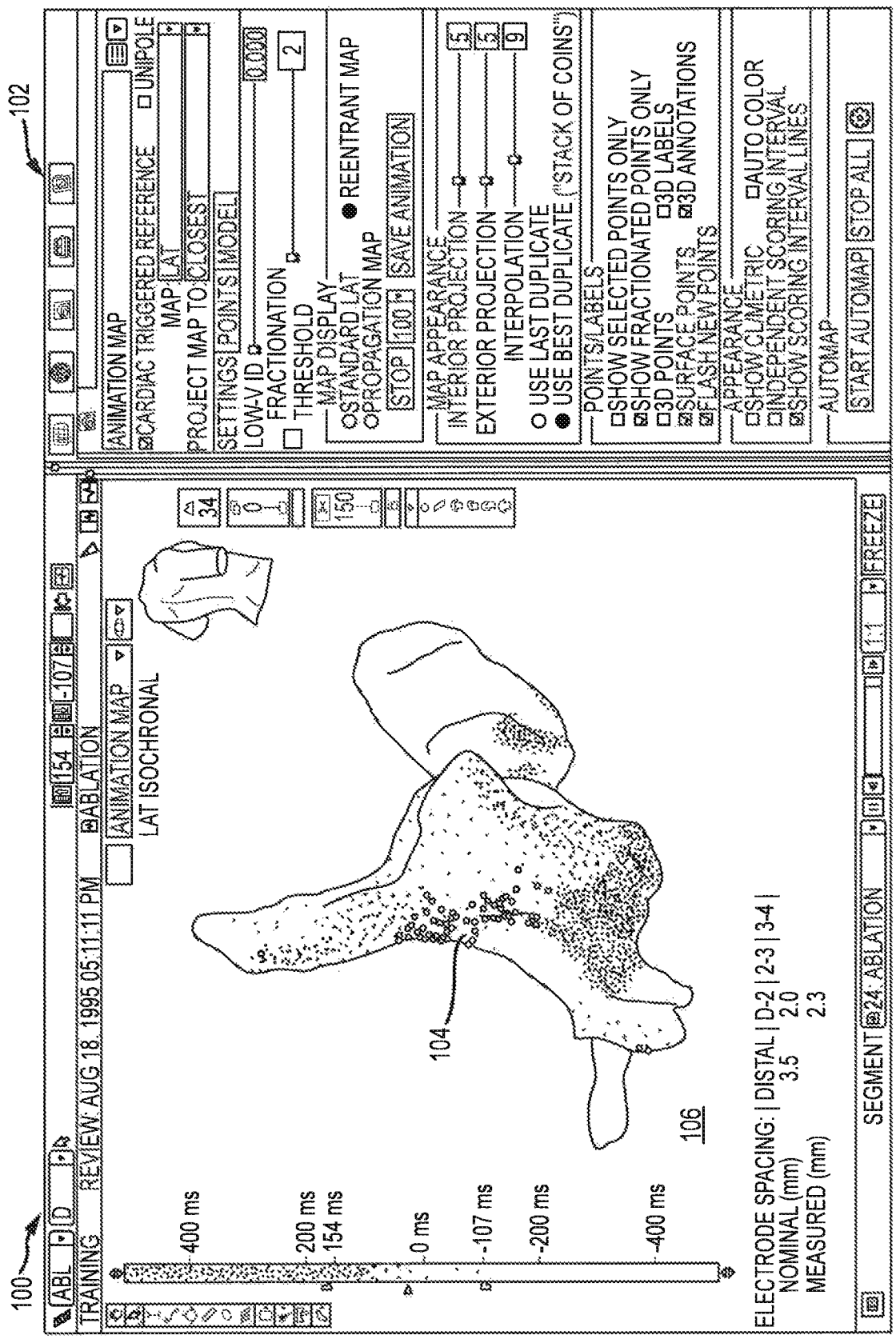
Figure 3F:
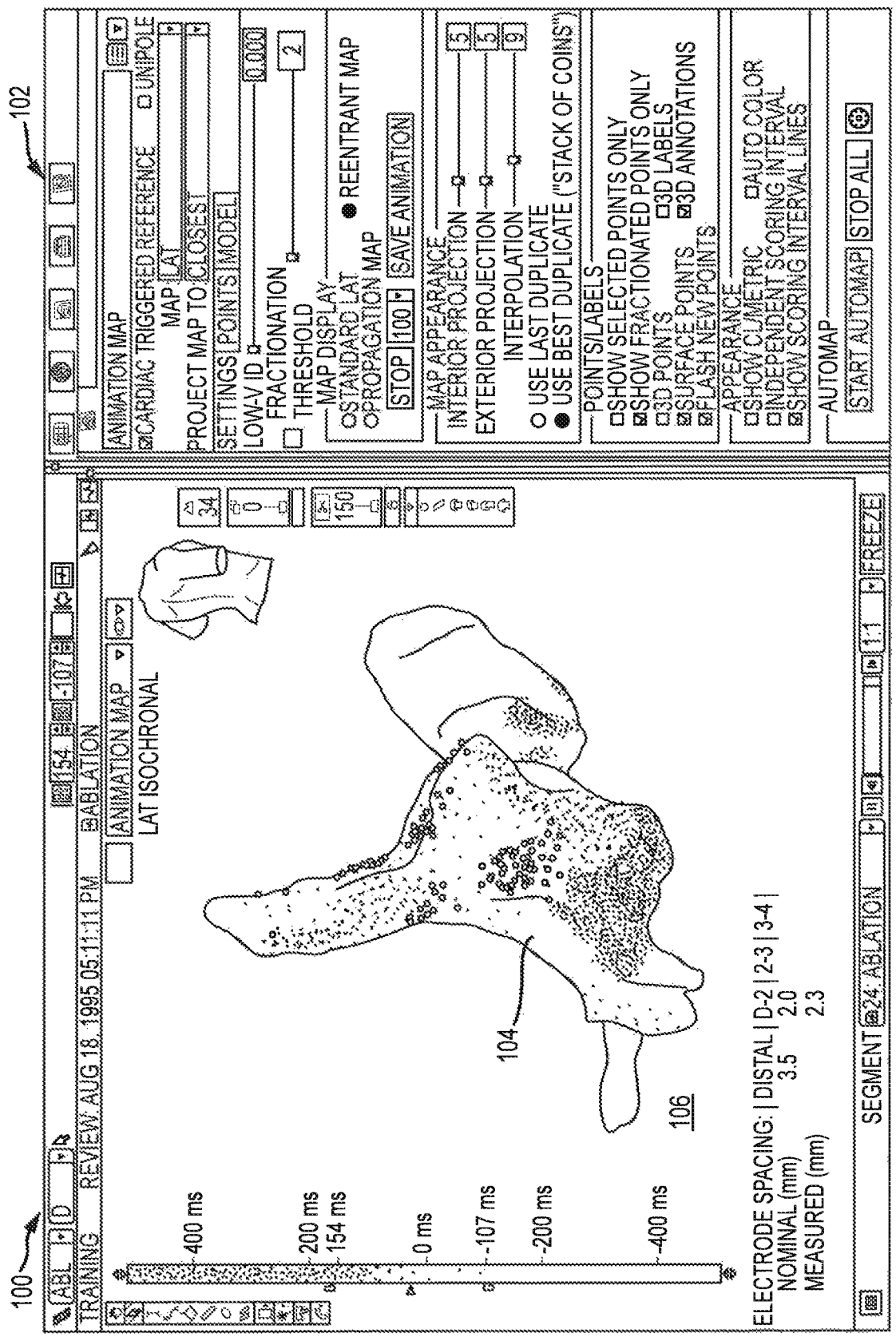
Figure 4A:
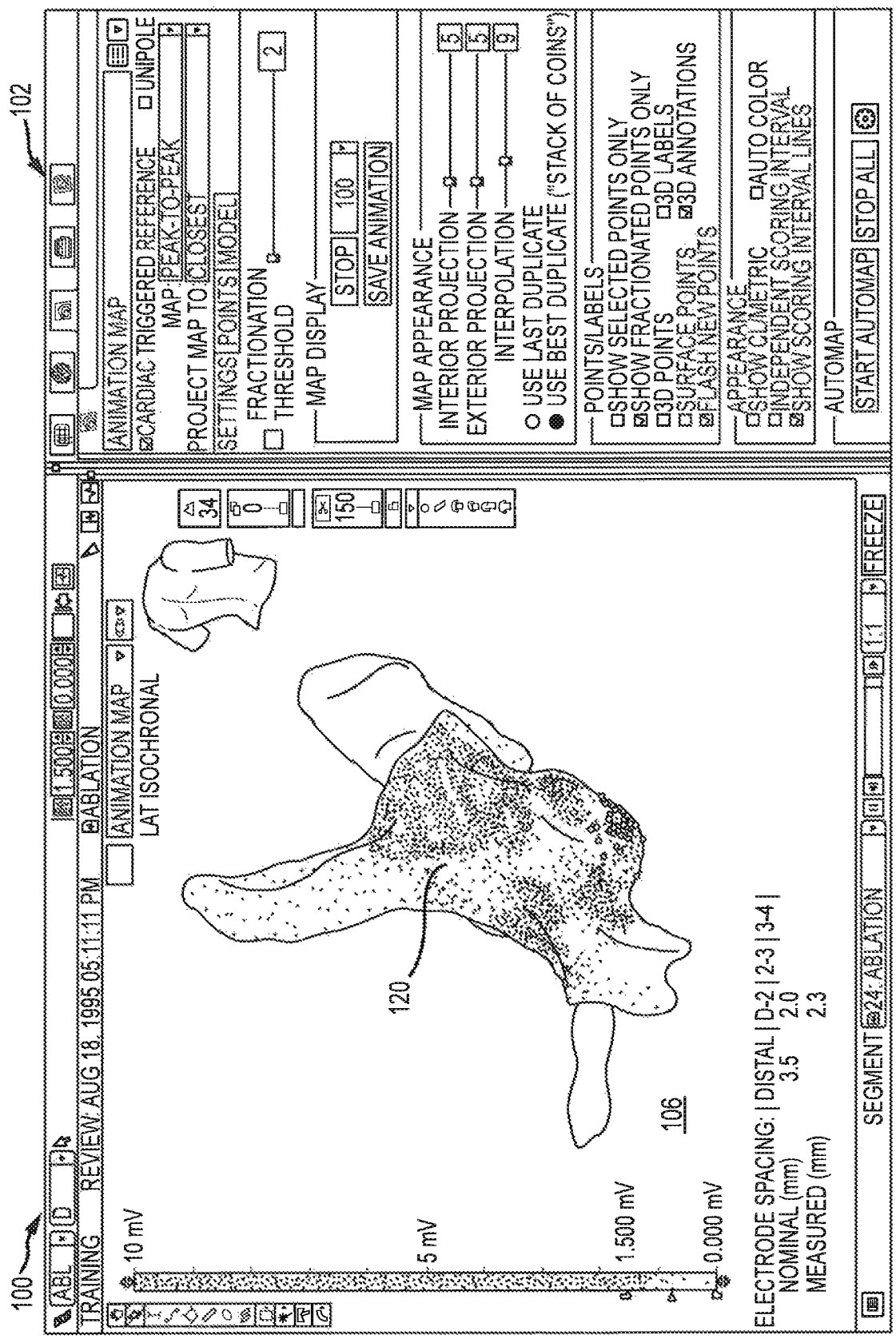
FIGS. 4A-4F are several screen shots of a graphical user interface used for generating an animated map by superimposing timing markers onto a peak-to-peak voltage map.
Figure 4B:
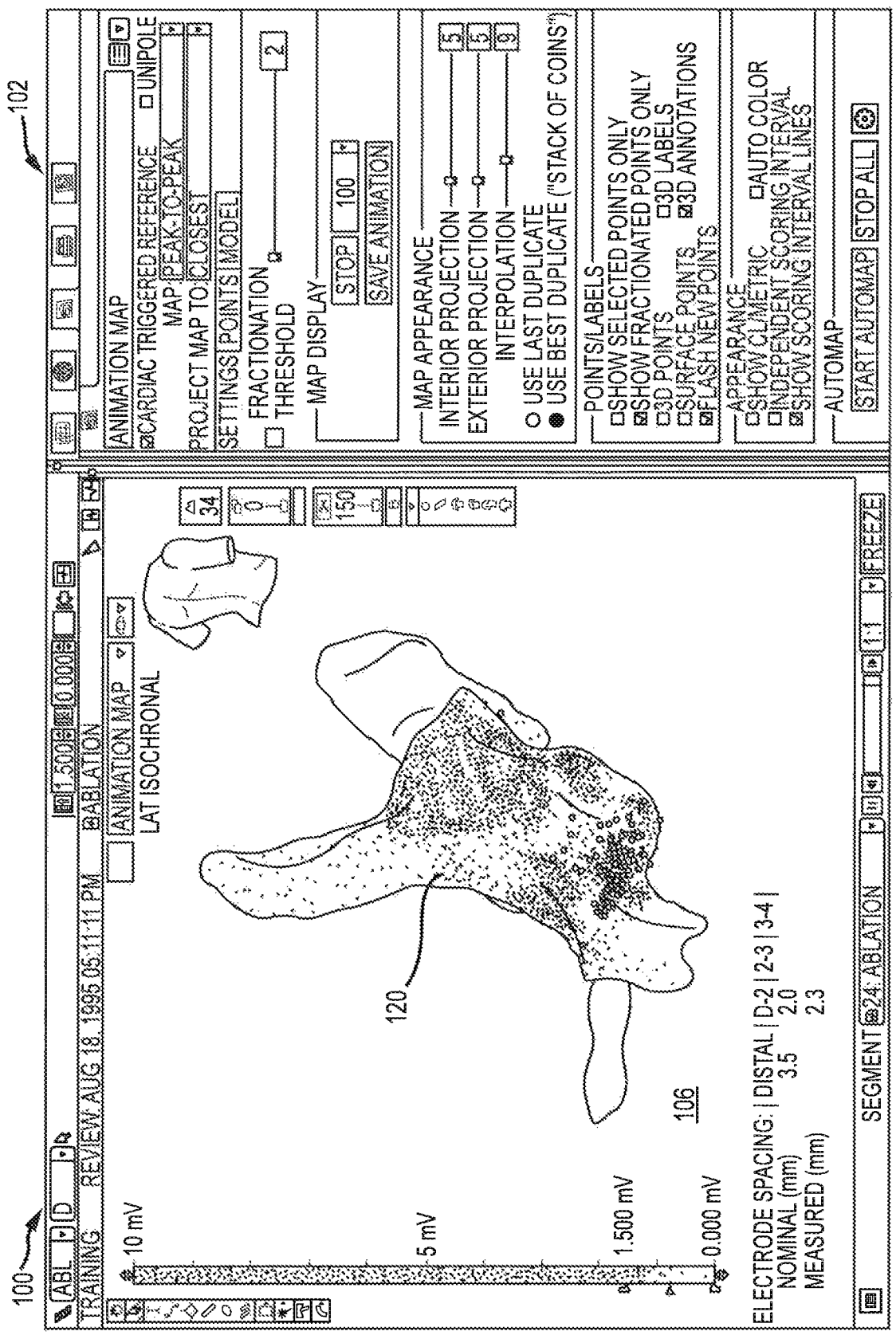
Figure 4C:
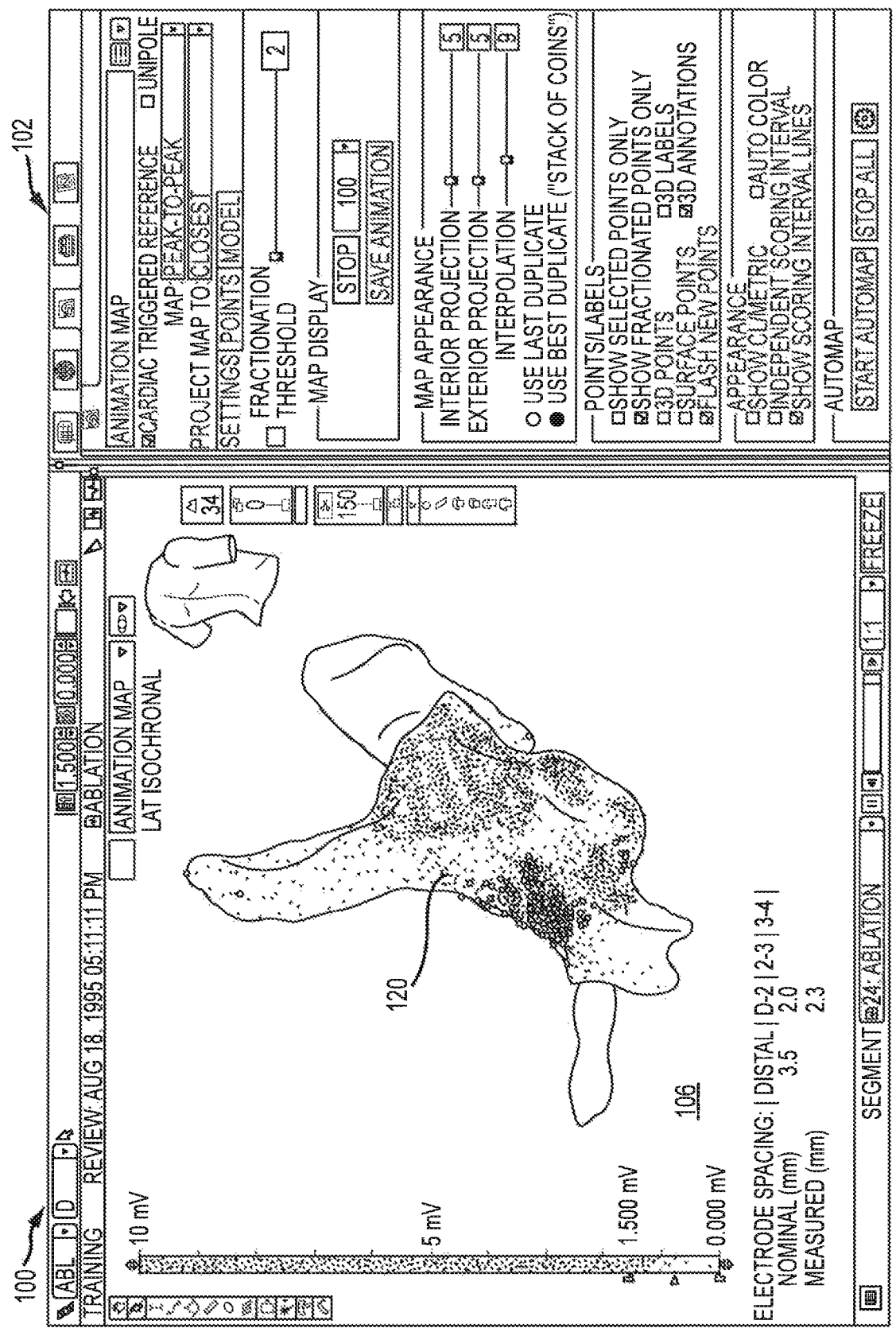
Figure 4D:
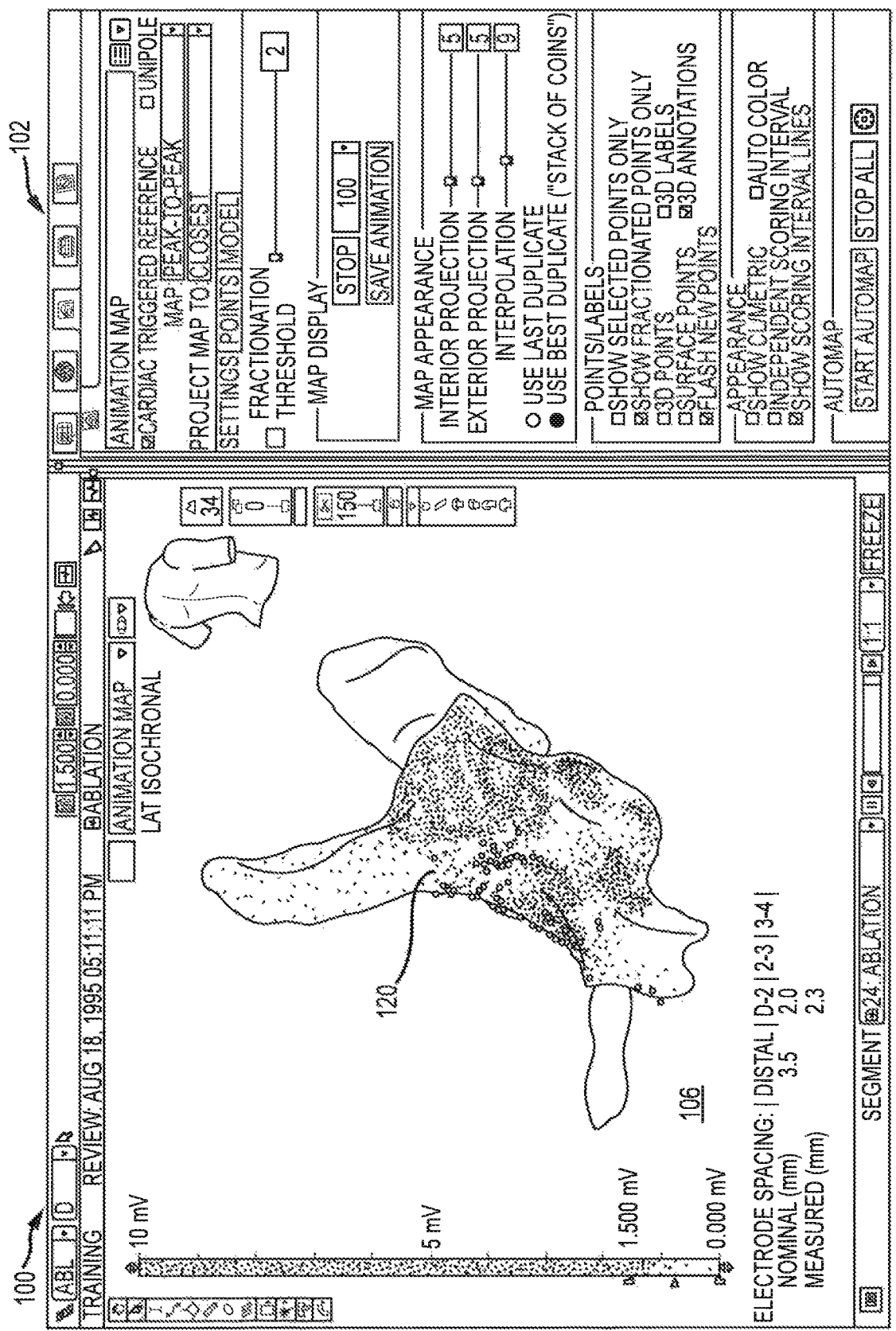
Figure 4E:
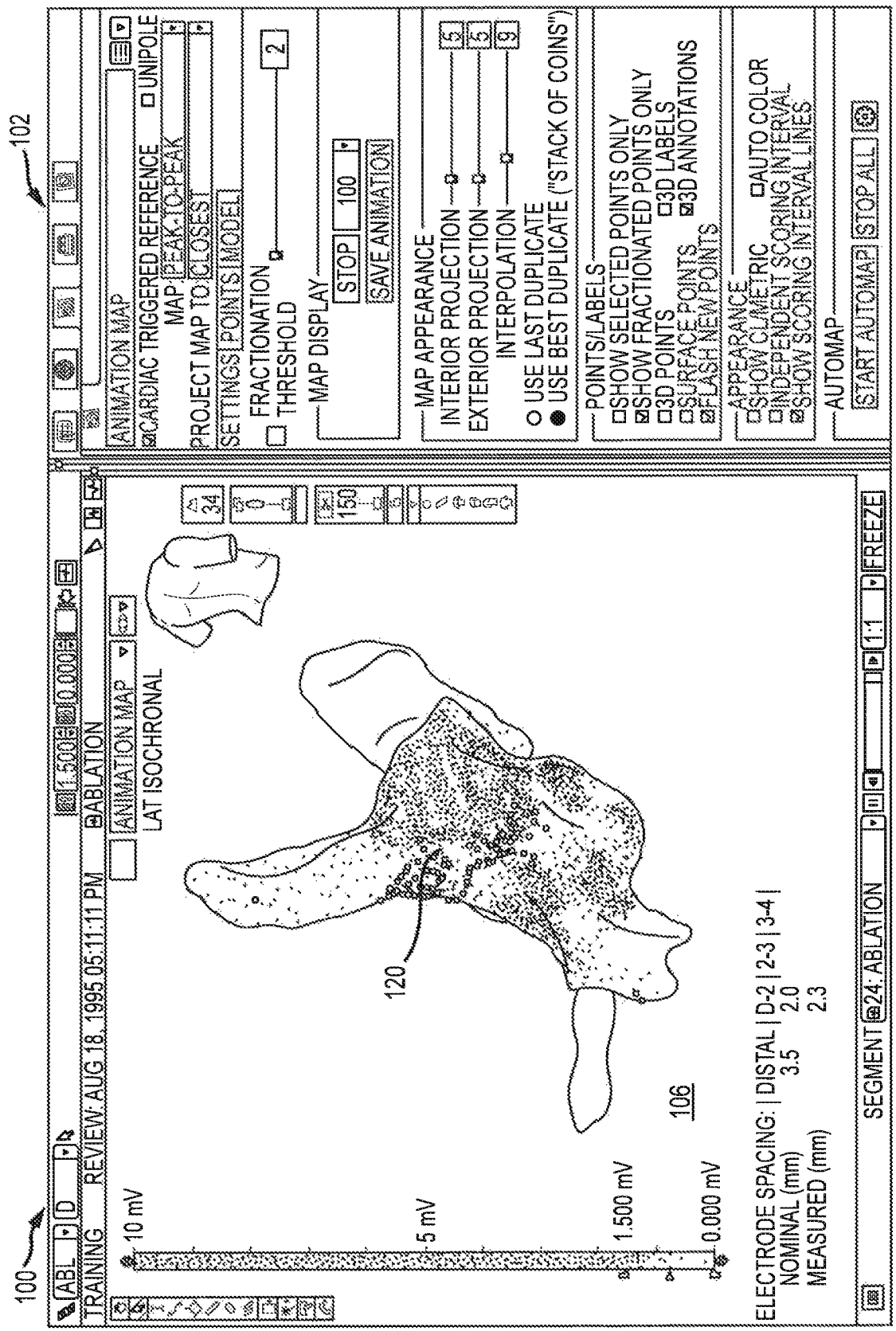
Figure 4F:
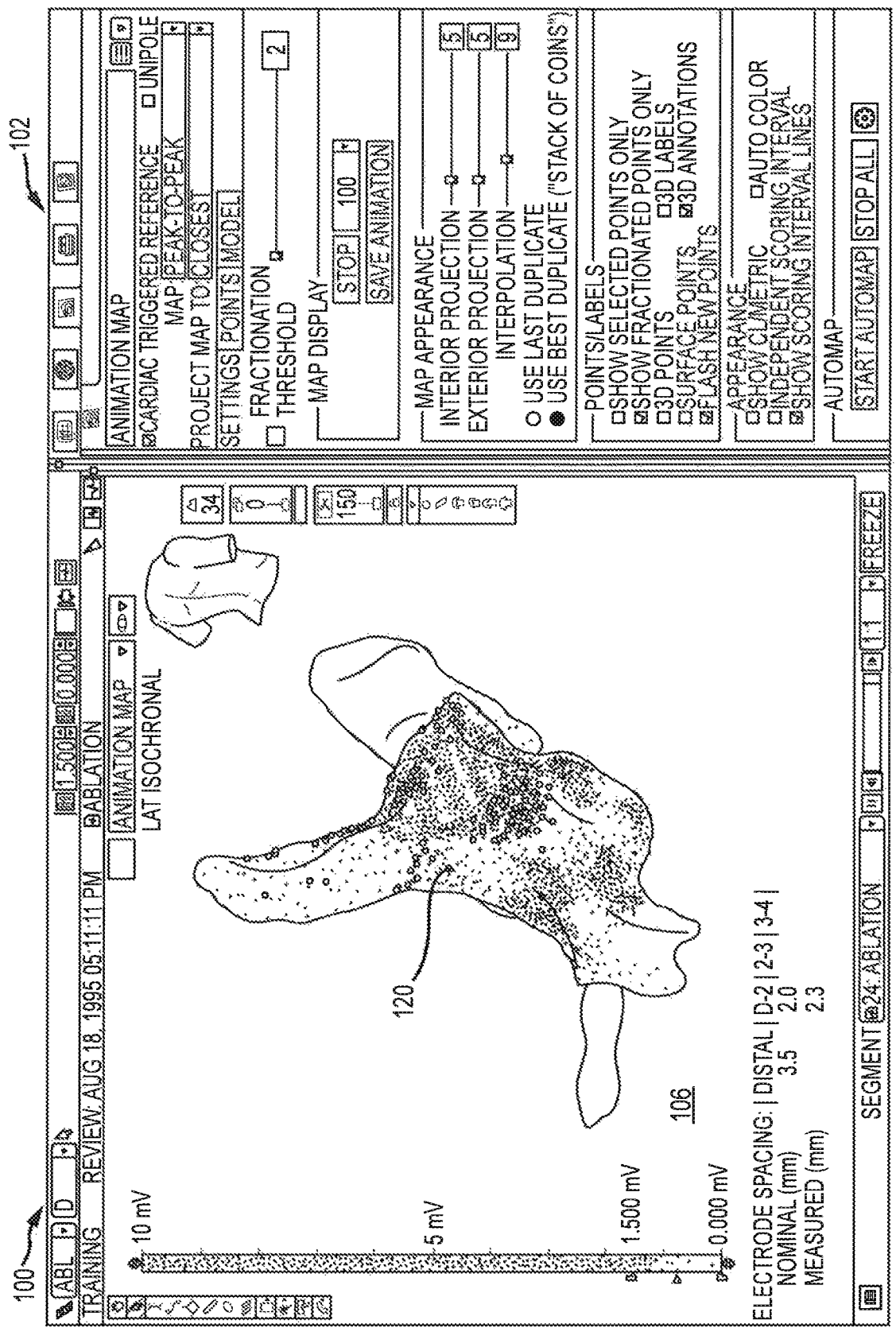
Figure 5A:
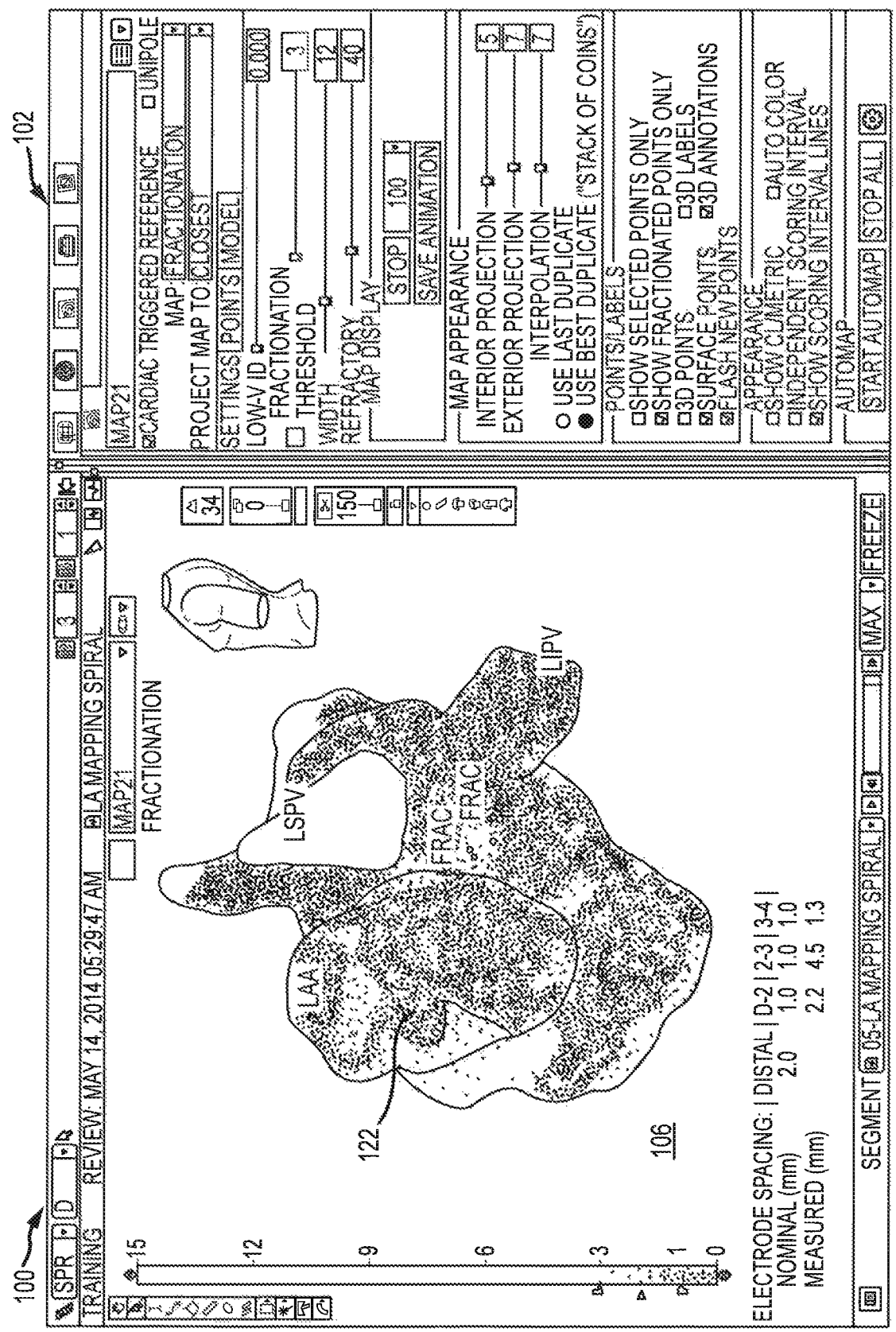
FIGS. 5A-5F are several screen shots of a graphical user interface used for generating an animated map by superimposing timing markers onto a fractionation map.
Figure 5B:
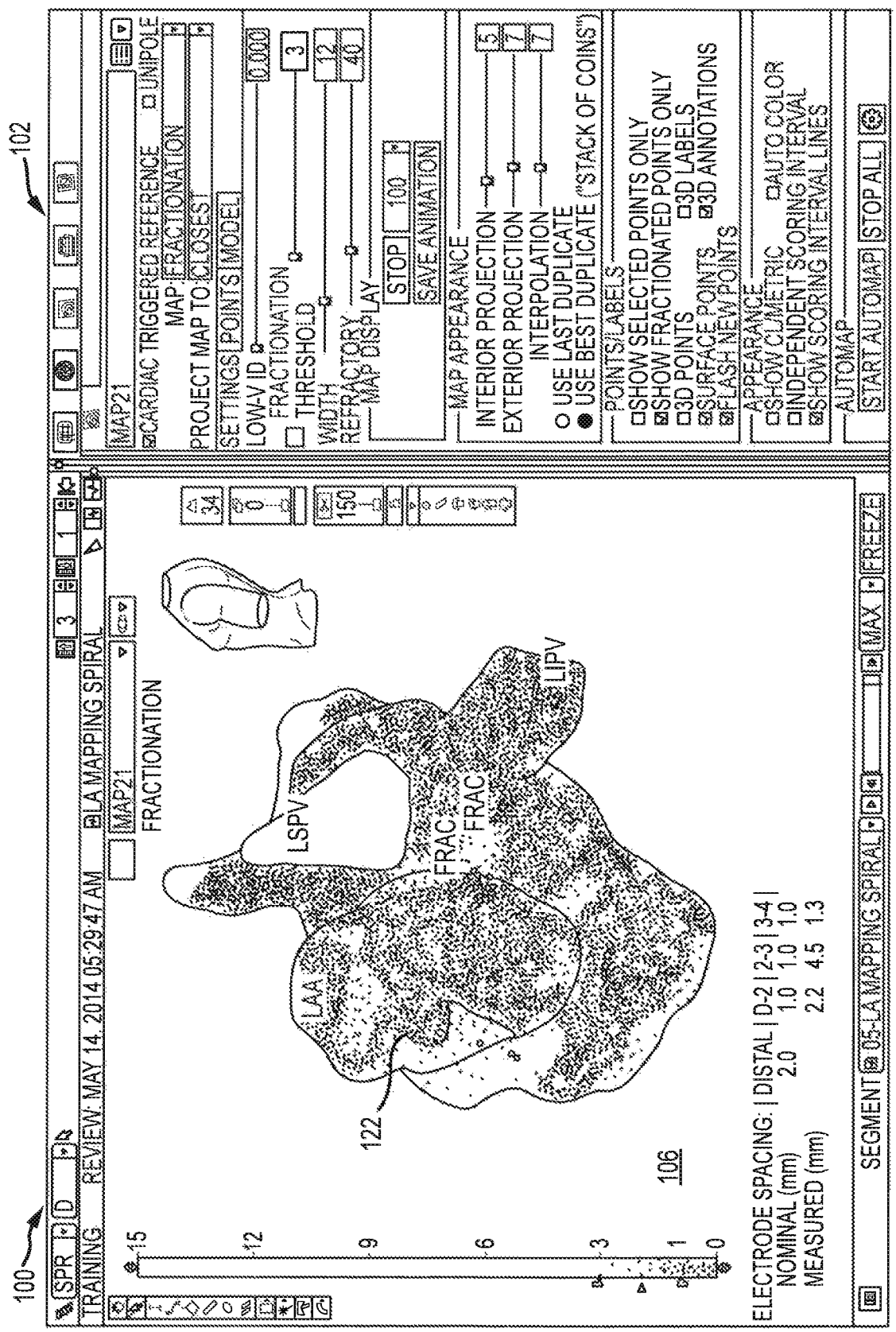
Figure 5C:
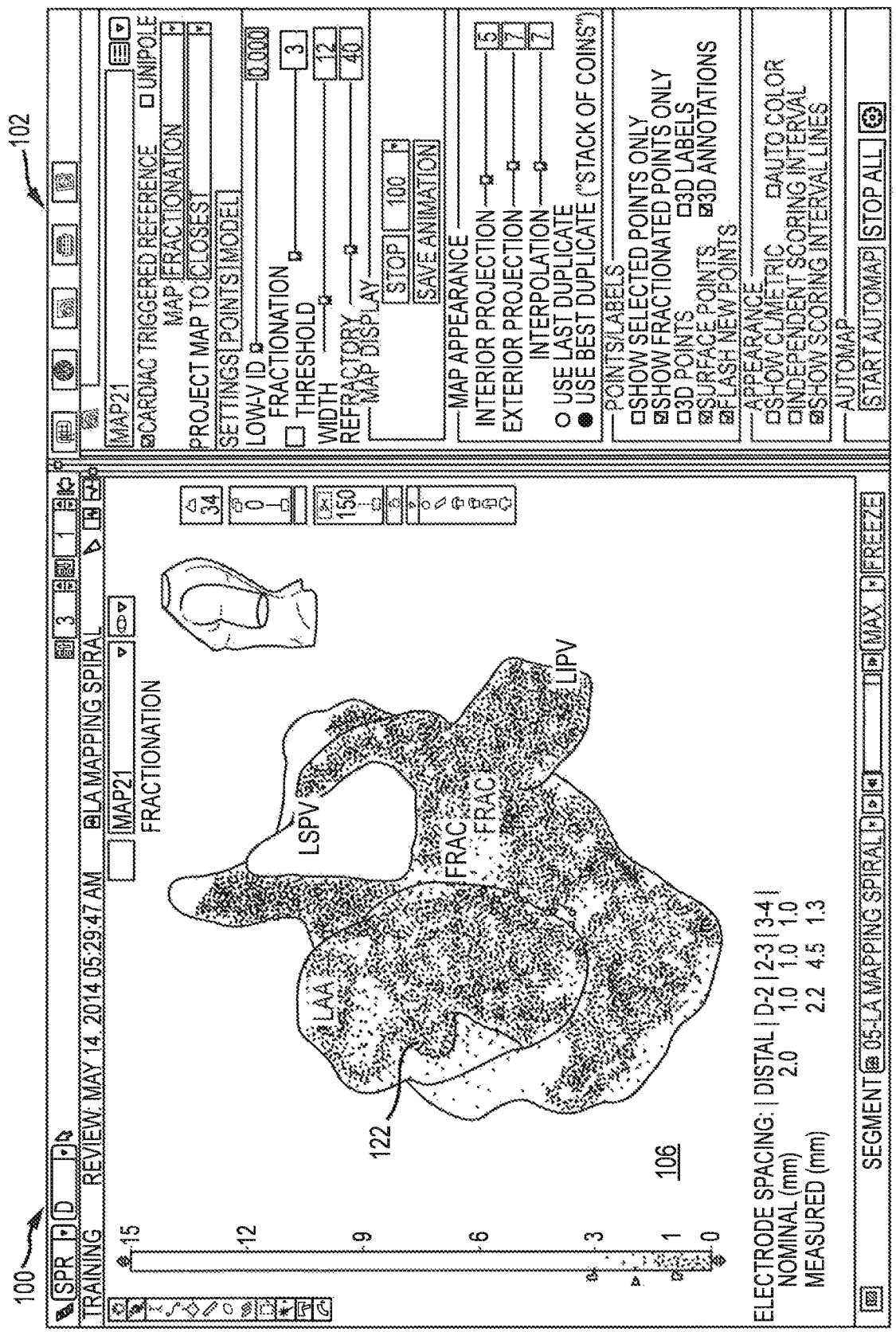
Figure 5D:
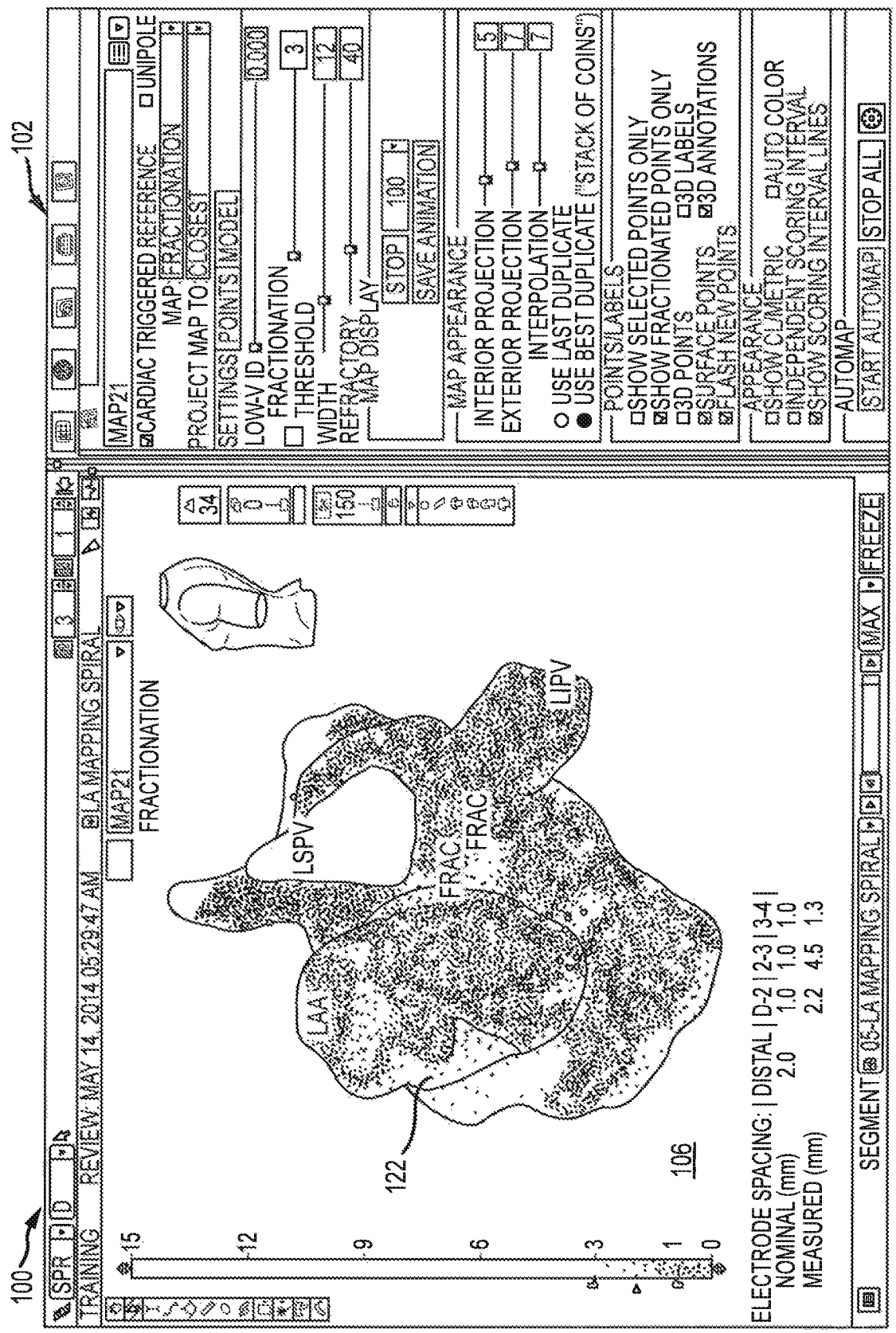
Figure 5E:
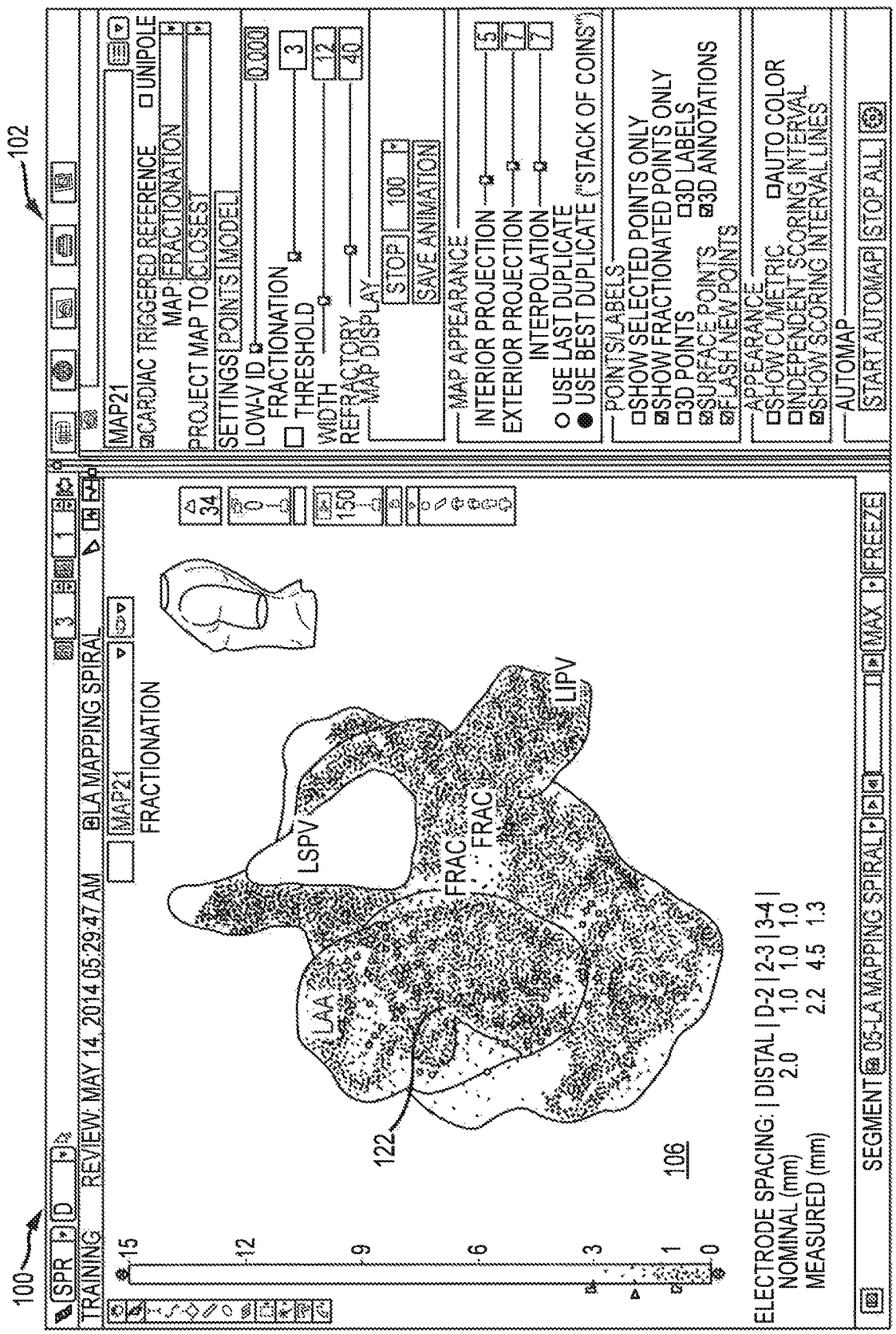
Figure 5F:
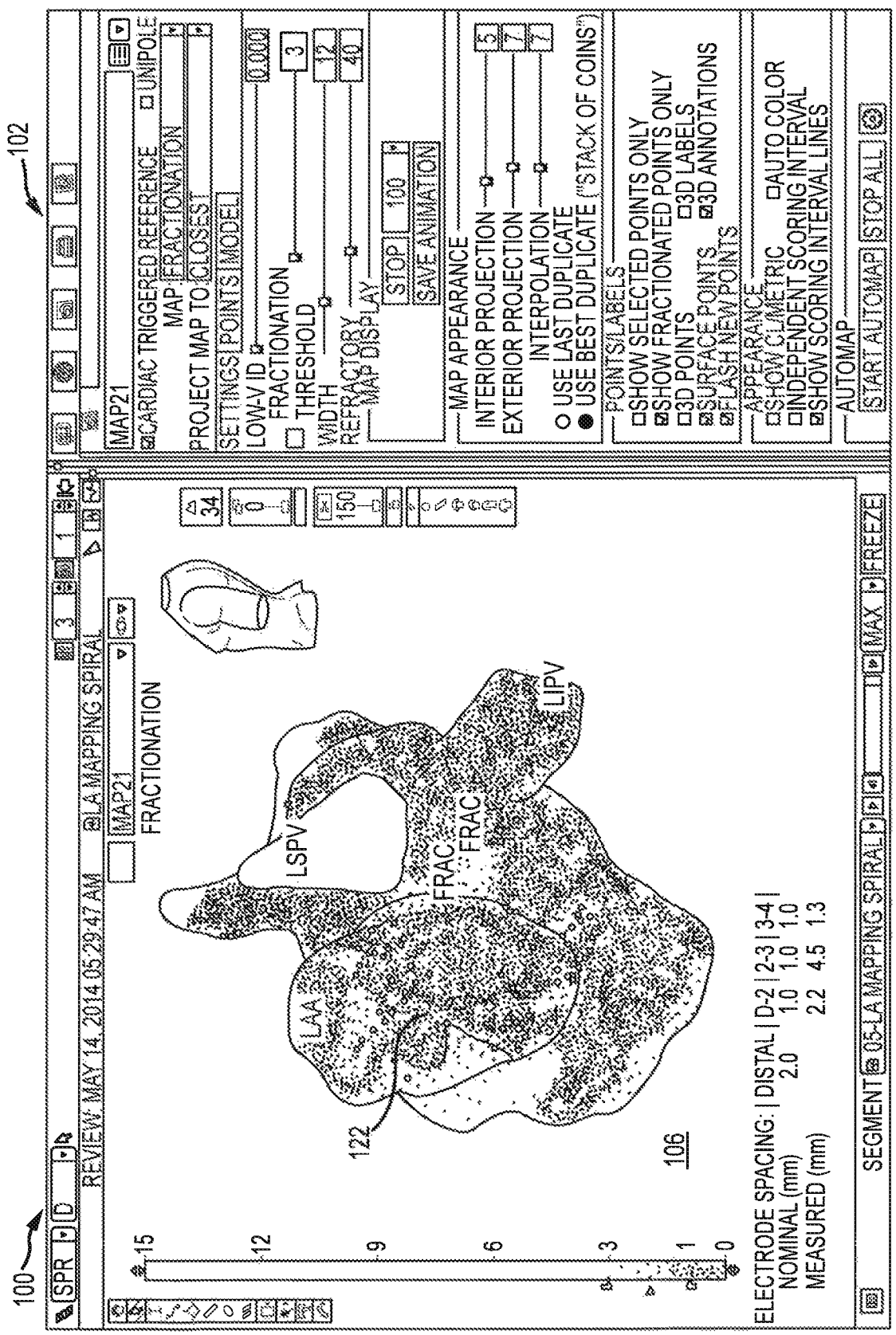

The process of adjusting the opacity of the timing markers 108 temporally and in sequence can be seen graphically by a comparison of FIGS. 3A-3F. Starting at an initial state in FIG. 3A which may represent the beginning of the cardiac cycle, for example, the system 8 may display timing markers 108a on the map. At a second time period, as shown in FIG. 3B by the difference in opacity depicted on the screen, the system 8 is configured to fade-out the timing markers 108a and conversely fade-in timing markers 108b. This process may be repeated one or more times (i.e., as shown in FIGS. 3C-3F) to generate additional frame sequences on the map 104. The generation of a sequence of frames in this manner provides a visual effect that the timing markers 110 are travelling across the map when, in fact, the different frames in the sequence are actually static.

From the example animation sequence in FIGS. 3A-3F, the clinician may deduce that the cardiac activation follows a path around a line of block. Activation patterns visualized in this manner can then be analyzed to determine the mechanism for an aberrant conduction and treat the condition, if desired. An example system and method for diagnosing arrhythmias and directing catheter therapies is disclosed in U.S. Pat. No. 9,186,081, the contents of which are incorporated herein by reference in their entirety for all purposes.

The system 8 can be configured to superimpose the timing markers 108 onto other electrophysiological maps to further facilitate the diagnosis and treatment of various arrhythmias. In another animation sequence shown in FIGS. 4A-4F, for example, the system 8 is configured to superimpose timing markers 108 onto a peak-to-peak voltage map 120. In another exemplary animation sequence shown in FIGS. 5A-5F, the system 8 is configured to superimpose the timing markers 108 onto a fractionation map 122 which shows the level or degree of fractionation in electrograms sensed at various locations on the surface of the heart. The system 8 can be configured to superimpose timing markers 108 onto other types of maps and/or onto multiple, composite maps types. In one embodiment, for example, the system 8 can be used to generate timing markers onto a map containing both an LAT map as well as a fractionation map. Other variations are also possible.

Figure 7:
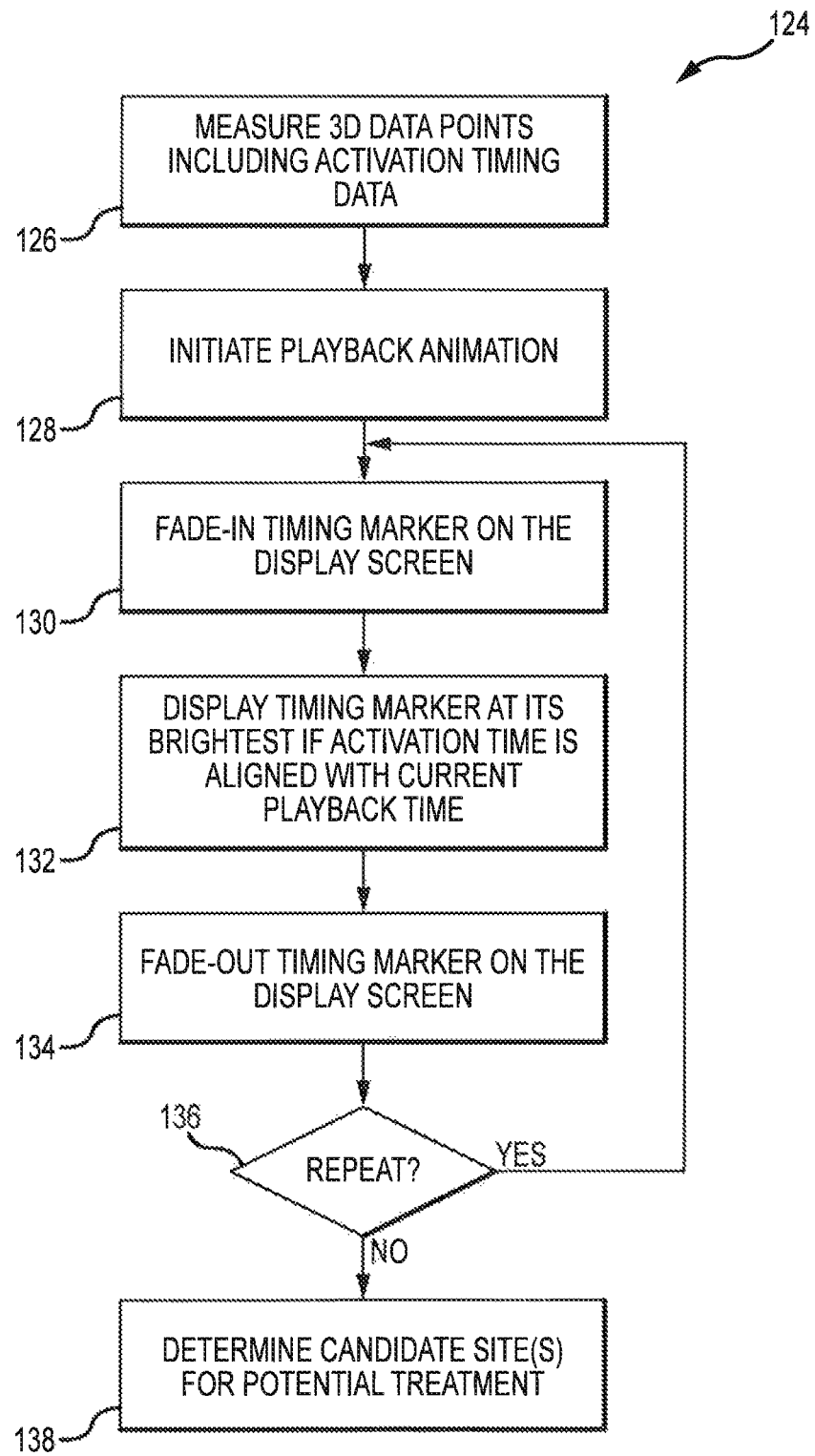
FIG. 7 is a flow diagram depicting several exemplary steps tier generating an animated map in accordance with an exemplary embodiment of the present disclosure.

FIG. 7 is a flow diagram showing several steps of an exemplary method 124 that can be used for superimposing an animated sequence of timing markers onto an electrophysiological map. The method 124 may begin generally at block 126, in which a mapping system and catheter are used to measure three dimensional data points on a surface of a heart, wherein the data points include associated activation timing data. Block 126 may represent, for example, the process of using the exemplary system 8 and catheter 13 described above with respect to FIGS. 1-2 to gather activation timing and voltage information at different locations on a model of the heart.

At block 128, a playback animation can be initiated (e.g., by the user via the selection of an icon button on the GUI) to generate a sequence of activation frames each containing an associated timing point for each three dimensional data point collected by the system 8. During each playback animation, the system 8 is configured to selectively display only those timing markers 108 that are associated with a time at or near the current playback time. As the time associated with the data point becomes more aligned with the current playback time, the system increases the opacity of the marker, causing the marker to be displayed initially as a shadow or silhouette on the display screen, as indicated generally at block 130. When the measured activation time is aligned with the current playback time, the timing marker is displayed at its brightest (block 132), providing the user with an indication of the location of the activation wavefront. Afterwards, the system 8 then decreases the level of opacity until that particular time marker is no longer visible on the screen, as indicated at block 134. The process is then repeated one or more times to create an animated sequence of frames that is superimposed over the map, as indicated at decision block 136. The clinician may then determine one or more candidate sites for potential treatment, as indicated at block 138.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating an animated electrophysiology map, the method comprising:
    receiving a plurality of data points, each data point comprising measured electrophysiology information, location information, and timing information;
    generating an electrophysiology map using the electrophysiology information and location information of the plurality of data points; and
    superimposing an animation of a plurality of timing markers upon the electrophysiology map using the electrophysiology information, the location information, and the timing information for the plurality of data points,
    wherein superimposing an animation of a plurality of timing markers upon the electrophysiology map comprises:
    generating a series of frames, each frame of the series of frames comprising:
        a static image of the electrophysiology map at a point in time; and
        one or more timing markers superimposed upon the static image of the electrophysiology map, wherein positions of the one or more timing markers upon the static image of the electrophysiology map correspond to a position of an activation wavefront on the electrophysiology map at the point in time, wherein the one or more timing markers are visible upon the static image of the electrophysiology map at the point in time only within a preset distance of the position of the activation wavefront on the electrophysiology map at the point in time, and wherein a visibility of a timing marker of the one or more timing markers is related to a distance between the position of the activation wavefront on the electrophysiology map at the point in time and a position of the timing marker on the electrophysiology map; and
    displaying the series of frames in chronological sequence.

2. The method according to claim 1, wherein an opacity of the timing marker is related to the distance between the position of the activation wavefront on the electrophysiology map at the point in time and the position of the timing marker on the electrophysiology map.

3. The method according to claim 1, wherein superimposing an animation of a plurality of timing markers upon the electrophysiology map comprises depicting an activation wavefront moving across the electrophysiology map over time.

4. The method according to claim 1, wherein superimposing an animation of a plurality of timing markers upon the electrophysiology map comprises:
increasing a visibility of a first timing marker from a minimum visibility to a maximum visibility;
decreasing the visibility of the first timing marker from the maximum visibility to the minimum visibility;
increasing a visibility of a second timing marker from the minimum visibility to the maximum visibility; and
decreasing the visibility of the second timing marker from the maximum visibility to the minimum visibility.

5. The method according to claim 4, wherein the steps of decreasing the visibility of the first timing marker and increasing the visibility of the second timing marker occur concurrently.

6. The method according to claim 4, wherein at least one of the step of increasing a visibility of a first timing marker and the step of increasing a visibility of a second timing marker occurs over a first time period.

7. The method according to claim 6, wherein at least one of the step of decreasing the visibility of the first timing marker and the step of decreasing the visibility of the second timing marker occurs over a second time period longer than the first time period.

8. The method according to claim 1, wherein the electrophysiology map comprises a local activation timing map.

9. The method according to claim 1, wherein the electrophysiology map comprises a peak-to-peak voltage map.

10. The method according to claim 1, wherein the electrophysiology map comprises a fractionation map.

11. The method according to claim 1, wherein the plurality of timing markers comprise a plurality of maximum voltage over time markers.

* * * * *